United States Patent
Panattoni

(10) Patent No.: US 7,056,426 B2
(45) Date of Patent: Jun. 6, 2006

(54) PRE-CAST ELECTROPHORESIS SLAB GELS WITH EXTENDED STORAGE LIFE

(75) Inventor: Cory M. Panattoni, Winters, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 10/623,480

(22) Filed: Jul. 18, 2003

(65) Prior Publication Data

US 2004/0140214 A1 Jul. 22, 2004

Related U.S. Application Data

(63) Continuation-in-part of application No. 10/346,681, filed on Jan. 17, 2003, now abandoned.

(51) Int. Cl.
*G01N 27/453* (2006.01)

(52) U.S. Cl. ........................... 204/469; 204/470
(58) Field of Classification Search ............... 204/469, 204/470, 466, 615, 616
See application file for complete search history.

(56) References Cited

U.S. PATENT DOCUMENTS

| | | | | | |
|---|---|---|---|---|---|
| 4,209,373 | A | * | 6/1980 | Bluestein et al. | 204/468 |
| 4,314,897 | A | * | 2/1982 | Monte et al. | 206/449 |
| 4,657,656 | A | * | 4/1987 | Ogawa | 204/469 |
| 4,699,705 | A | * | 10/1987 | Ogawa et al. | 204/469 |
| 4,737,259 | A | * | 4/1988 | Ogawa et al. | 204/606 |
| 4,806,434 | A | * | 2/1989 | Ogawa | 204/470 |
| 4,891,119 | A | * | 1/1990 | Ogawa | 204/469 |
| 4,963,243 | A | * | 10/1990 | Ogawa et al. | 204/469 |
| 5,464,516 | A | * | 11/1995 | Takeda et al. | 204/456 |
| 5,753,095 | A | * | 5/1998 | Alpenfels et al. | 204/616 |
| 5,837,288 | A | * | 11/1998 | Sylvester et al. | 424/484 |
| 5,938,906 | A | * | 8/1999 | Moi et al. | 204/465 |

* cited by examiner

*Primary Examiner*—Kaj K. Olsen
(74) *Attorney, Agent, or Firm*—Townsend and Townsend and Crew LLP

(57) ABSTRACT

In pre-cast slab gel cassettes, the formation of pathways in which proteins can migrate between the gel and the walls of the cassette to form shadow bands is avoided by including a nonionic amphiphilic polymer in the monomer solution from which the gel is formed and casting the gel with the polymer included. The nonionic amphiphilic polymer also prevents the resulting gel from sticking to the walls when the gel is to be removed from the cassette after electrophoresis.

19 Claims, No Drawings

PRE-CAST ELECTROPHORESIS SLAB GELS WITH EXTENDED STORAGE LIFE

CROSS REFERENCE TO RELATED APPLICATION

This patent application is a continuation-in-part of U.S. patent application Ser. No. 10/346,681, filed Jan. 17, 2003, now abandoned the contents of which are incorporated herein by reference in their entirety, as are all literature citations in this specification.

BACKGROUND OF THE INVENTION

1. Field of the Invention

This invention relates to polyacrylamide gels as used in slab gel electrophoresis.

2. Description of the Prior Art

When electrophoresis is performed in a slab gel, several samples can be analyzed simultaneously in the same gel and the resulting electropherograms can be observed and read visually by identifying the locations of the bands on the gel that correspond to the individual components. Polyacrylamide is a gel material that is widely used in slab gels.

Slab gels are frequently supplied in pre-cast form in cassettes that typically contain two flat transparent plates with the gel retained between them. The plates may be glass or plastic, one commonly used plastic being a polystyrene-acrylonitrile blend. A difficulty with certain pre-cast polyacrylamide gels is that during storage the gels appear to separate from the cassette plates. This creates a pathway between the gel and one or both of the plates in which the sample can migrate during electrophoresis. This migration causes shadow bands in the electropherogram which obscure the clarity and identification of the parent bands, i.e., those that are formed as a direct result of the electrophoretic separation. Shadow bands occur most frequently in pre-cast gels that have been stored without cooling.

Another problem encountered with polyacrylamide slab gels is a tendency of the gels to stick or adhere to the plates. This presents a difficulty once the separation is completed and the gel must be removed from the plates for purposes of staining, photographing or other observation, detection or recordation. Attempts to remove a gel that is sticking to one or both of the plates can result in a damaged gel and a ruined experiment. This problem is especially acute for gels of low concentration and for gels used for isoelectric focusing.

The polymerization reaction to form polyacrylamide is inhibited when dissolved oxygen is present in the gel-forming liquid at or near the gel plate. This is especially true when the gel plates are plastic, such as polystyrene-acrylonitrile, for example. To prevent this inhibition from occurring, a coating of polyvinylidene chloride or polyvinyl dichloride (PVDC) is often applied to the plates prior to contacting the plates with the polyacrylamide gel material. Unfortunately, these coatings exacerbate the sticking problem when the gel is an isoelectric focusing gel, for example one with a pH ranging from 5 to 8. In addition, electrophoresis images produced both with and without these coatings often contain irregularities that appear to be the result of a separation between the gel and the plate.

SUMMARY OF THE INVENTION

The present invention resides in the discovery that both the occurrence of shadow bands due to apparent pathways between a polyacrylamide gel and a gel cassette plate and the adherence of the gel to the plate can be prevented by forming the gel from a monomer solution that includes a nonionic amphiphilic polymer in addition to the monomers. The polymer is added to the solution before the gel is cast, and casting is then performed with the polymer still present.

DETAILED DESCRIPTION OF THE INVENTION AND PREFERRED EMBODIMENTS

Examples of nonionic amphiphilic polymers that can be used in the practice of this invention are poly(vinyl alcohol), agarose, poly(vinyl pyrrolidone), poly(ethylene glycol), poly(ethylene oxide), poly(propylene glycol), poly(propylene glycol)/poly(ethylene glycol) copolymers, and linear polyacrylamide. These polymers are fully formed prior to being added to the gel-forming solution, are soluble in the gel-forming solution, and do not have sites available for crosslinking reactions. Preferred polymers are those having molecular weights of about 100,000 to about 8,000,000, particularly those in the range of about 100,000 to about 5,000,000, and even more particularly those in the range of about 100,000 to about 1,000,000. In certain embodiments of the invention, lower molecular weight polymers are used, for example those having molecular weights of about 100,000 or less, particularly those with molecular weights of about 20,000 or less, more particularly those within the range of about 200 to about 20,000, and still more particularly those with molecular weights within the range of about 200 to about 5,000. The weight percent of the polymer in the monomer solution can range widely, although lowering the molecular weight tends to permit equivalent or similar results with higher weight percents of the polymer. In the case of polyvinyl alcohol, for example, a preferred concentration range is from about 0.5% to about 5% by weight of the monomer solution. When poly(ethylene glycol) or poly(ethylene oxide) is used, a preferred concentration is from about 0.01% to about 0.3% by weight. The concentrations and molecular weights of other nonionic amphiphilic polymers are readily determined by routine experimentation and will in many cases be readily apparent to those skilled in the art.

The gel-forming solution is an aqueous solution of a monomer mixture that is polymerizable, generally by a free-radical reaction, to form polyacrylamide. Any monomer mixture that has been used or is described in the literature as being useful in forming polyacrylamide gels can be used in the practice of this invention. The monomer mixture typically includes acrylamide, a crosslinking agent, and a free radical initiator. Preferred crosslinking agents are bisacrylamides, and a particularly convenient crosslinking agent is N,N'-methylene-bisacrylamide.

The gel-forming solution will also typically include a free radical initiator system. The most common system used is N,N,N',N'-tetramethylenediamine (TEMED) in combination with ammonium persulfate. Other systems will be apparent to those skilled in the art. The gel-forming solution can also contain additional components that are known or used in electrophoresis gels for various reasons. Buffering agents are commonly included since electrophoretic separations are typically performed at designated pH values. Density control agents, such as glycerol, are also useful in many systems, particularly when the resolving gel is formed underneath a stacking gel.

Among those skilled in the use of electrophoresis and the preparation of electrophoresis gels, polyacrylamide gels are characterized by the parameters T and C, which are expressed as percents and defined as follows (in which "bis" denotes the bisacrylamide crosslinker):

$$T = \frac{\text{(combined weight of acrylamide and bis in grams)}}{\text{(volume of aqueous solution in mL)}} \times 100$$

$$C = \frac{\text{(weight of bis)}}{\text{(combined weight of acrylamide and bis)}} \times 100$$

The values of T and C can vary in the present invention as they do in the use of polyacrylamide gels in general. For the purposes of the present invention, a preferred range of T values is from about 3% to about 30%, and most preferably from about 5% to about 20%. A preferred range of C values of from about 1% to about 10% (corresponding to a range of weight ratio of acrylamide to bisacrylamide of from about 10:1 to about 100:1), and most preferably from about 2% to about 4% (corresponding to a range of weight ratio of acrylamide to bisacrylamide of from about 25:1 to about 50:1).

The invention is applicable to gels of uniform concentration as well as gradient gels. The methods for forming both uniform and gradient gels are well known in the art.

The plates that form the gel cassette are chemically inert, transparent materials, either glass or plastic or both. A wide variety of plastics can be used. The plastics are generally injection moldable plastics, and the selection is limited only by the need for the plastic to be inert to the gel-forming solution, the gel itself, the solutes (typically proteins) in the samples to be analyzed in the cassette, the buffering agents, and any other components that are typically present in the samples. Examples of these plastics are polycarbonate, polystyrene, acrylic polymers, styrene-acrylonitrile copolymer (SAN, NAS), BAREX® acrylonitrile polymers (Barex Resins, Naperville, Ill., USA), poly(ethylene terephthalate) (PET), poly(ethylene terephthalate glycolate) (PETG), and poly(ethylene naphthalenedicarboxylate) (PEN).

The following examples are offered for illustrative purposes and are not intended to limit the scope of the invention.

EXAMPLE 1

This example illustrates the preparation of a gradient gel containing poly(ethylene glycol) as a nonionic amphiphilic polymer gel additive in accordance with the present invention.

Three aqueous gel-forming solutions to be used in the formation of a gradient gel were prepared as follows (all percents by weight):

Solution A:
acrylamide/N,N'-methylene-bisacrylamide (T=21%, C=2.6%)
10% glycerol
0.1% TEMED
0.0375% polyethylene glycol, weight-average molecular weight 200–1,000

Solution B:
acrylamide/N,N'-methylene-bisacrylamide (T=6%, C=2.6%)
0.2% TEMED
0.0375% polyethylene glycol, weight-average molecular weight 200–1,000

Solution C:
1.125 M tris-HCl (tris(hydroxymethyl)aminomethane hydrochloride), pH 8.6
0.15% ammonium persulfate A slab gel cassette formed from two styrene-acrylonitrile plastic plates was used, with a gel space measuring 13.4 cm×8.4 cm×1 mm. A gel was formed inside the cassette by first pumping a mixture of Solution B and Solution C at a volume ratio of two-thirds B to one-third C into the cassette from the bottom, to achieve a T=4% stacking gel solution with a PEG concentration of 0.025% by weight. A gradient gel was then formed under the stacking gel by pumping a mixture of Solutions A, B, and C at varying amounts of A and B into the cassette under the 4% gel solution. A ratio of two parts by volume of A plus B to one part by volume of C was maintained while the volume ratio of A to B was varied to produce a T gradient extending from 10.5% to 14%.

EXAMPLE 2

This example illustrates the preparation and use of uniform (non-gradient) gels containing poly(ethylene glycol) of molecular weight 200 as the gel additive in accordance with the present invention.

Slab gels were prepared from gel-forming solutions identical to Solution A of Example 1, except with T=11.25% and with the inclusion in some of the gels of poly(ethylene glycol), weight-average molecular weight 200 (Sigma PEG 200), at a concentration of 0.022% by weight. The gel dimensions were identical to those of Example 1. Electrophoretic separations were run on the gels, utilizing a broad molecular-weight range protein standard from Bio-Rad Laboratories, Inc. (Hercules, Calif. USA), consisting of a selection of nine proteins with molecular weights ranging from 6,500 to 200,000, of which five are resolvable by a typical Tris-HCl gel. The separations were run with a voltage of 200 V, using a running buffer containing tris-glycine sodium dodecyl sulfate at approximately 35° C. for approximately 55 minutes. Separations under these conditions were performed on gels immediately after casting and also on gels that had been stored for 6 days at 37° C.

Among the gels that did not contain PEG, protein bands on gels where separation was performed after 6 days of storage were compared with protein bands on a gel that was used immediately after preparation. The protein bands on the 6-day gels had noticeable trailing regions extending downstream of the parent bands, and all bands were blurred, both indicating deterioration of the gels. By contrast, the protein bands on the fresh gel were sharply defined and had no trailing regions.

The protein bands on the gels that contained the 0.022% PEG 200 demonstrated a similar difference between the 6-day gels and the fresh gel, but with less intensity. The trailing regions were about half the darkness of those observed in the 6-day gels that did not contain PEG, and the band sharpness was noticeably improved.

EXAMPLE 3

This example is another illustration of the preparation and use of uniform (non-gradient) gels containing poly(ethylene glycol) of molecular weight 1,000 as the gel additive in accordance with the present invention.

Various slab gels were prepared as in Example 2, again using 0.22% PEG 200, with a storage time of 5 days rather than 6. All other materials, procedures, and conditions were the same.

Among the gels that did not contain PEG, the gels that were used after 5 days of storage were compared with a fresh gel. Bands corresponding to two of the five proteins in the standard had trailing regions on the 5-day gels as compared with no trailing regions on the fresh gel. Shadow bands also appeared on the 5-day gels that did not appear on the fresh gel, the slowest migrating bands were smeared, and all bands on the 5-day gels were blurred in comparison to the sharp bands on the fresh gel.

The protein bands on the gels that contained PEG demonstrated much less difference between the 5-day gels and the fresh gel. No trailing regions were present, no shadow bands, and the smearing was eliminated, although some blurring still remained.

EXAMPLE 4

This example illustrates the preparation and use of uniform (non-gradient) gels containing poly(ethylene glycol) of molecular weight 10,000 as the gel additive in accordance with the present invention.

Various slab gels were prepared as in Example 2, except that PEG with weight-average molecular weight 10,000 (Sigma PEG 10000) at a concentration of 0.044 weight % was used, and the storage time was 7 days. All other materials, procedures, and conditions were the same.

A difference was observed between the fresh gels without PEG and the fresh gels with PEG 10000. Bands representing three or four proteins in the latter were sharper and thinner than the bands for the same proteins in the former. Differences were also observed between the 7-day gels with and without PEG. Smearing of the bands for two of the proteins that appeared in the gels without PEG did not appear in the gels with PEG.

EXAMPLE 5

This example illustrates the use of poly(ethylene glycol) of molecular weight 20,000 as the gel additive in accordance with the present invention.

Various slab gels were prepared as in the preceding examples, except that PEG with weight-average molecular weight 20,000 (Sigma PEG 20000) at a concentration of 0.044 weight % was used, and the storage time was 7 days. All other materials, procedures, and conditions were the same.

A comparison between the fresh gels without PEG and the fresh gels with PEG 10000 revealed that edge waviness on the bands of two of the proteins that appeared in the gels without PEG did not appear in the gels with PEG. A comparison between the seven-day gels revealed that trailing regions appearing on bands associated with one of the proteins in the PEG-free gels were eliminated in the PEG-containing gels, and smearing of the bands associated with two of the proteins in the PEG-free gels was eliminated in the PEG-containing gels. The 7-day PEG-containing gels also included a sharp band that was not visible in the 7-day PEG-free gels.

EXAMPLE 6

This example illustrates the use of poly(ethylene glycol) of molecular weight 35,000 as the gel additive in accordance with the present invention.

Slab gels were prepared as in the preceding examples, except that PEG with weight-average molecular weight 35,000 (Sigma PEG 20000) at a concentration of 0.022 weight % was used, with a storage time of 6 days. All other materials, procedures, and conditions were the same.

A comparison between the fresh gels without PEG and the fresh gels with PEG 10000 revealed a small amount of smearing and blurring of the bands in the gels with PEG as compared to those without PEG. A comparison between the 6-day gels revealed that trailing regions appearing on bands associated with three of the proteins in the PEG-free gels were either eliminated or reduced by about 80% in the PEG-containing gels, and smearing of the bands associated with one of the proteins in the PEG-free gels was eliminated in the PEG-containing gels.

EXAMPLE 7

This example illustrates the use of poly(ethylene oxide)s (as identified by the suppliers) of molecular weights 116,000, 205,000, 400,000, and 438,000 in separate experiments as the gel additive in accordance with the present invention.

Slab gels were prepared as in the preceding examples, using the poly(ethylene oxide)s (PEOs) cited in the preceding paragraph, all at a concentration of 0.022 weight %, with a storage time of 6 days. All other materials, procedures, and conditions were the same.

A comparison between the fresh gels without PEO and the fresh gels with PEO at the various molecular weights revealed that the sharpest protein bands were in the gels containing the PEO of 438,000 molecular weight, with the sharpness of the bands increasing as the PEO molecular weight increased. Comparisons among the 6-day gels revealed a similar progression, with band sharpness again increasing as the PEO molecular weight increased.

EXAMPLE 8

This example is another illustration of the use of poly (ethylene oxide)s as the gel additive in accordance with the present invention, this time using molecular weights of 511,000, 600,000, 1,000,000, 5,000,000, and 8,000,000.

Slab gels were prepared as in the preceding examples, using the PEOs cited in the preceding paragraph, all at a concentration of 0.022 weight %, with a storage time of 7 days. All other materials, procedures, and conditions were the same.

A comparison between the fresh gels without PEO and the fresh gels with PEO at the various molecular weights revealed that the sharpest and straightest protein bands were in the gels containing the PEO of 600,000 molecular weight, with the sharpness of the bands decreasing and waviness appearing as the poly(ethylene oxide) molecular weight increased above 600,000, the waviness becoming greater with increasing molecular weight. Comparisons among the 7-day gels revealed a similar optimum at 600,000 molecular weight. The 7-day gels with this PEO had shorter and lighter trailing regions than those with no PEO, but the trailing regions darkened as the poly(ethylene oxide) molecular weight increased. With poly(ethylene oxide)s of increasing molecular weights, the resulting bands had an increasing waviness in appearance, possibly due to the increasing viscosity of the monomer solutions. This increasing viscosity may have interfered with the mixing of the monomer and buffer solutions (A and C or B and C).

The foregoing description is primarily for purposes of illustration. Further modifications, substitutions and variations will be apparent to those skilled in the art and will be included within the scope of the invention.

What is claimed is:

1. A method for manufacturing a pre-cast polyacrylamide slab gel for use in slab electrophoresis, said method comprising:

(a) placing a gel-forming liquid mixture inside a gel enclosure defined by a pair of chemically inert, transparent plates separated from each other by fixed distance, said gel-forming mixture comprising an acrylamide monomer, a crosslinking agent, a buffer, and a nonionic amphiphilic polymer, in aqueous solution; and (b) polymerizing said gel-forming mixture into a gel;

wherein the nonionic amphiphilic polymer is selected from polyethylene oxide and polyethylene glycol in a concentration of from about 0.01 to about 0.3% by weight.

2. A method in accordance with claim 1 in which said nonionic amphiphilic polymer has a molecular weight of from about 100,000 to about 8,000,000.

3. A method in accordance with claim 1 in which said nonionic amphiphilic polymer has a molecular weight of from about 100,000 to about 5,000,000.

4. A method in accordance with claim 1 in which said nonionic amphiphilic polymer has a molecular weight of from about 100,000 to about 1,000,000.

5. A method in accordance with claim 1 in which said nonionic amphiphilic polymer has a molecular weight of about 100,000 or less.

6. A method in accordance with claim 1 in which said nonionic amphiphilic polymer has a molecular weight of about 20,000 or less.

7. A method in accordance with claim 1 in which said plates are glass.

8. A method in accordance with claim 1 in which said plates are plastic.

9. A method in accordance with claim 8 in which said plastic is a member selected from the group consisting of polycarbonate, polystyrene, acrylic polymers, styrene-acrylonitrile copolymer, acrylonitrile polymers, poly(ethylene terephthalate), poly(ethylene terephthalate glycolate), and poly(ethylene naphthalenedicarboxylate).

10. A method in accordance with claim 8 in which said plastic is a polystyrene-acrylonitrile blend.

11. A pre-cast polyacrylamide slab gel for use in slab gel electrophoresis, said pre-cast slab gel comprising:

a pair of chemically inert, transparent plates, and a polyacrylamide gel cast between said plates, said polyacrylamide gel formed by polymerization of an acrylamide monomer and a crosslinking agent, said polymerization having been performed in an aqueous solution comprising said acrylamide monomer, said crosslinking agent, a buffer, and a nonionic amphiphilic polymer, wherein the nonionic amphiphilic polymer is selected from polyethylene oxide and polyethylene glycol in a concentration of from about 0.01 to about 0.3% by weight.

12. A pre-cast polyacrylamide slab gel in accordance with claim 11 in which said nonionic amphiphilic polymer has a molecular weight of from about 100,000 to about 8,000,000.

13. A pre-cast polyacrylamide slab gel in accordance with claim 11 in which said nonionic amphiphilic polymer has a molecular weight of from about 100,000 to about 5,000,000.

14. A pre-cast polyacrylamide slab gel in accordance with claim 11 in which said nonionic amphiphilic polymer has a molecular weight of from about 100,000 to about 1,000,000.

15. A pre-cast polyacrylamide slab gel in accordance with claim 11 in which said nonionic amphiphilic polymer has a molecular weight of about 20,000 or less.

16. A pre-cast polyacrylamide slab gel in accordance with claim 11 in which said plates are glass.

17. A pre-cast polyacrylamide slab gel in accordance with claim 11 in which said plates are plastic.

18. A pre-cast polyacrylamide slab gel in accordance with claim 17 in which said plastic is a member selected from the group consisting of polycarbonate, polystyrene, acrylic polymers, styrene-acrylonitrile copolymer, acrylonitrile polymers, poly(ethylene terephthalate), poly(ethylene terephthalate glycolate), and poly(ethylene naphthalenedicarboxylate).

19. A pre-cast polyacrylamide slab gel in accordance with claim 17 in which said plastic is a polystyrene-acrylonitrile blend.

* * * * *